United States Patent
Abbott, Jr. et al.

(10) Patent No.: US 9,557,288 B2
(45) Date of Patent: Jan. 31, 2017

(54) ELECTROCHEMICAL SENSING WELL

(71) Applicant: Hewlett-Packard Development Company, L.P., Houston, TX (US)

(72) Inventors: James Elmer Abbott, Jr., Albany, OR (US); Greg Scott Long, Corvallis, OR (US); Michael A. Delos-Reyes, Covallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 615 days.

(21) Appl. No.: 13/873,199

(22) Filed: Apr. 29, 2013

(65) Prior Publication Data

US 2014/0318957 A1   Oct. 30, 2014

(51) Int. Cl.
| | | |
|---|---|---|
| *C23C 14/00* | (2006.01) | |
| *C23C 14/32* | (2006.01) | |
| *G01N 27/403* | (2006.01) | |
| *C23C 14/34* | (2006.01) | |

(52) U.S. Cl.
CPC ............. *G01N 27/403* (2013.01); *C23C 14/34* (2013.01)

(58) Field of Classification Search
CPC .............................. C23C 14/34; G01N 27/403
See application file for complete search history.

(56) References Cited

U.S. PATENT DOCUMENTS

| | | | |
|---|---|---|---|
| 7,771,926 B2 | 8/2010 | Petyt et al. | |
| 8,080,152 B2 | 12/2011 | Sirringhaus | |
| 2002/0090649 A1* | 7/2002 | Chan ................... | B01J 19/0046 435/7.1 |
| 2006/0171654 A1* | 8/2006 | Hawkins ............... | G01N 21/05 385/147 |
| 2012/0047964 A1 | 3/2012 | Chang et al. | |
| 2012/0056943 A1 | 3/2012 | Nielsen et al. | |
| 2012/0109010 A1* | 5/2012 | Sato ..................... | A61B 5/1411 600/583 |
| 2012/0181185 A1 | 7/2012 | Vitushinsky et al. | |

OTHER PUBLICATIONS

T. E. McKnight et al.; Microarrays of Vertically-aligned Carbon Nanofiber Electrodes in an Open Fluidic Channel; May 1, 2004; pp. 7115-7125.
Winters, Shane, Multiple Lateral Field Excited Sensors on a Single Substrate, Theses, Aug. 2011, 5pgs.,Univ. of Maine.

* cited by examiner

*Primary Examiner* — Ibrahime A Abraham
(74) *Attorney, Agent, or Firm* — Rathe Lindenbaum LLP

(57) ABSTRACT

A well is formed in a body of dielectric material and has a chamfered edge about a top side of the well. A top electrode layer is on a top face of the body and on the chamfered edge of the well. A bottom electrode is on a floor of the well.

11 Claims, 15 Drawing Sheets

ELECTROCHEMICAL SENSING WELL

BACKGROUND

Electrochemical analysis is sometimes used to identify particular chemical species in a liquid analyte having a fixed concentration of a particular chemical species and/or a fixed volume, which may be in the milliliter range. The field of electrochemical analysis may be advanced by a lower-cost sensing system that facilitates more efficient analysis utilizing, for instance, reduced analyte size and/or reagent consumption.

DETAILED DESCRIPTION OF THE EXAMPLE EMBODIMENTS

Figure 1:
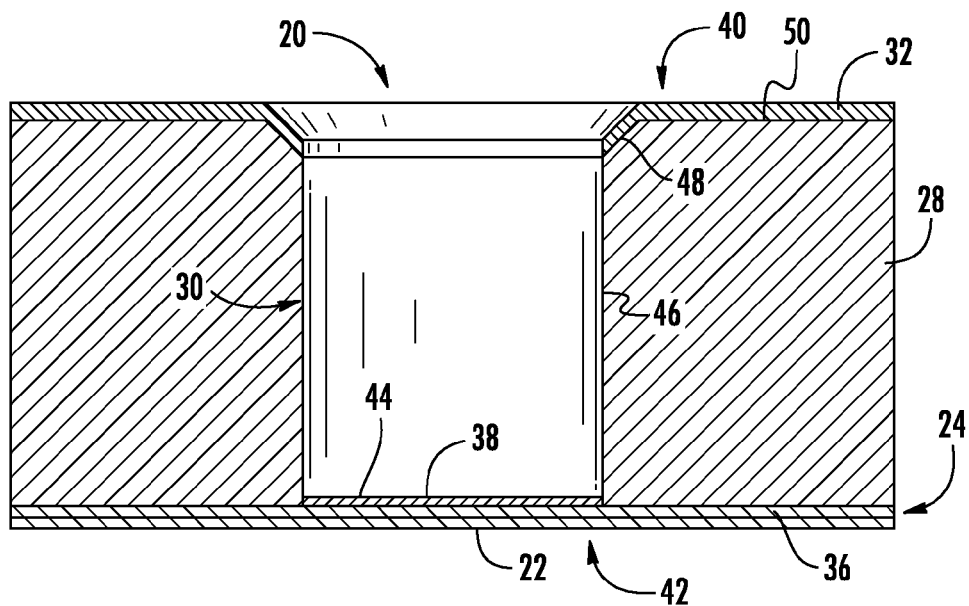
FIG. 1 is a sectional view of an example electrochemical sensing cell.

FIG. 1 is a sectional view illustrating an example electrochemical sensing cell 20. Cell 20 is configured to contain an individual analyte undergoing electrochemical analysis. Although illustrated as a single cell, cell 20 may be incorporated as part of a larger array of cells 20. As will be described hereafter, cell 20 facilitates a high precision high-volume manufacture of an array of such cells 20 into which analytes of chemicals in liquid or biological fluids may be easily introduced. Cell 20 further facilitates new methods of chemical sensing, smaller form factors, lower chemical consumption for analysis and lower cost for a given capability.

Cell 20 comprises substrate 22, bottom electrode 24, body 28, well 30 and top electrode 32. Substrate 22 comprises a base, platform, panel, plate or other foundational structure upon which a remainder of cell 20 is supported. Substrate 22 comprises at least one layer of dielectric material. In one implementation, substrate 22 comprises one or more layers of flexible dielectric materials provided from a roll, facilitating a roll-to-roll manufacturing or fabrication process. In one implementation, substrate 22 may comprise a layer of one or more polymers. In other implementations, substrate 22 may be formed from other materials and may have other configurations. In some implementations, substrate 22 may be omitted.

Bottom electrode 24 comprises an electrically conductive structure in electrical connection with a bottom or floor of well 30 so as to apply an electrical charge to a liquid analyte contained within well 30. In the example illustrated, bottom electrode 24 comprises bottom electrode portion 36 and well electrode portion 38. Bottom electrode portion 36 comprises a layer of electrically conductive material, such as a metal or indium tin oxide, formed upon and supported by substrate 22. In one implementation, bottom electrode portion 36 comprises one or more electrically conductive traces. In another implementation, bottom electrode portion 36 comprises a sheet or panel of electrically conductive material.

Well electrode portion 38 comprises that portion of electrode 24 serving as an electrical contact to the liquid analyte within well 30. In one implementation, well electrode portion 38 is formed concurrently with the formation of top electrode 32. In some implementations, well electrode portion 38 may be omitted, wherein portions of bottom electrode portion 36 serve as an electrical contact for a liquid analyte within well 30.

Body 28 comprises a mass of dielectric material adjacent bottom electrode 36. Body 28 provides a volume of dielectric material in which well 30 is formed. Body 28 further supports top electrode 32. In one implementation, body 28 is formed from a dielectric embossable material such as an embossing resin. In other implementations, body 28 may be formed from other materials.

Well 30 comprises a hole, bore, depression, open topped receptacle or open topped reservoir extending into body 28 from a topside 40 towards a bottom side 42 of body 28. In one implementation, well 30 is one of an array of such wells formed in body 28. In one implementation, well 30 has a microscopic scale volume (having a height and/or breadth of 50 μm or less), reducing analyte size and reagent consumption. In another implementation, well 30 may have a macroscopic scale volume.

Well 30 comprises a floor 44, vertical sidewalls 46 and chamfer 48. Floor 44 extends along a bottom of well 30. In one implementation, the entirety of floor 44 is provided by electrode 24. In another implementation, portions of floor 44 are provided by electrode 24.

Sidewalls 46 extend upward from floor 44 substantially perpendicular to floor 44, bottom electrode 24 and substrate 22. In one implementation, sidewalls 46 have a circular cross sectional shape. In another implementation, sidewalls 46 have an elliptical cross sectional shape, a polygonal cross sectional shape or another cross sectional shape. For example, in other implementations, in lieu of comprising a cylinder, each of wells 30 may comprise a hexagon, a square, a rectangle, a triangle or any other shape forming an open topped volume for containing a liquid analyte or sample. The surfaces of sidewall 46 are formed or provided by the dielectric material of body 28. As a result, the dielectric surface of sidewall 46 electrically separate bottom electrode 24 from top electrode 32.

Chamfer 48 comprises a surface about a perimeter of well 30 that extends oblique to both sidewalls 46 and top surface 50 of body 28. Chamfer 48 comprises a sloped surface extending between sidewall 46 and top surface 50. Chamfer 48 forms a portion of the interior of well 30 at a top of well 30. Chamfer 48 provides a surface that at least partially faces in an upward direction such that top electrode 32 may be formed by directional deposition in a direction perpendicular to floor 44 and top surface 50, wherein the directionally deposited top electrode 32 is formed on chamfer 48 so as to be able to contact the liquid analyte within well 30 and is not formed on sidewalls 46 providing electrical isolation of bottom electrode 24 and top electrode 32.

In one implementation, chamfer 48 extends at a 45° angle with respect to sidewalls 46 and top surface 50 of body 28. In another implementation, chamfer 48 may extend at other angles oblique to sidewall 46. In the example illustrated in which well 30 comprises a cylindrical bore, chamfer 48 has a circular cross sectional shape. In other implementations in which well 30 comprises a polygonal cross sectional shape or elliptical cross sectional shape, chamfer 48 may have other corresponding cross-sectional shapes.

Top electrode 32 comprise a layer of electrically conductive material formed on top surface 50 of body 28 and on chamfer 48 of well 30. In one implementation, top electrode 32 comprise a metal layer. In another implementation, top electrode 32 comprise a layer of indium tin oxide or other electrically conductive material. In one implementation, top electrode 32 comprises a continuous sheet on top surface 50 of body 28 and chamfer 48. In another implementation, top electrode 32 may comprise a patterned layer of electrically conductive material on top surface 50 so as to form one or more electric conductive traces. In one implementation, top electrode 32 is formed by directional deposition such as sputtering or evaporation. Top electrode 32 and bottom electrode 24 are configured so as to be connectable to a voltage source and an analytical device, facilitating the establishment of an electrical potential across or between electrodes 24, 32 and facilitating electrochemical analysis, such as through the analysis of impedance of the liquid analyte within well 30.

Figure 2:
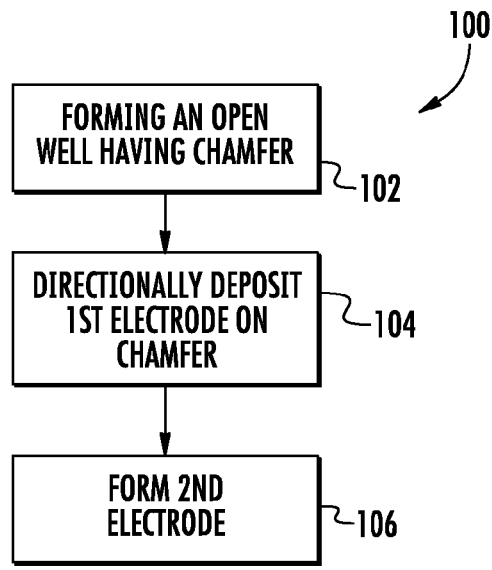
FIG. 2 is a flow diagram of an example method for forming the electrochemical sensing cell of FIG. 1.

FIG. 2 is a flow diagram of an example method 100 for forming electrochemical sensing cell 20. As indicated by step 102, well 30 having chamfer 48 is formed in body 28. As described hereafter, various methods for forming well 30 with chamfer 48 and body 28 may be utilized. In one implementation, well 30 may be formed by embossing. In another implementation, well 30 may be formed by photo imaging or other material removal techniques. In one implementation, sidewalls 46 and chamfer 48 are formed concurrently. In another implementation, sidewalls 46 and chamfer 48 are formed in distinct steps.

As indicated by step 104, electrode 32 is formed by directionally depositing an electrically conductive material, such as a metal or indium tin oxide, on the top surface 50 of body 28 and on chamfer 48 of well 30. In one implementation, electrode 32 is formed by directional deposition such as sputtering or evaporation. The electrically conductive material forming electrode 32 is deposited in a direction perpendicular to top surface 50 of body 28 and parallel to sidewalls 46 of well 30 such that electrically conductive material is not deposited upon sidewalls 46. As a result, sidewalls 46 electrically separate or isolate bottom electrode 24 from top electrode 32.

As indicated by step 106, the second or bottom electrode 24 is formed. In one implementation, bottom electrode 24 is formed in a two-part process, wherein portion 36 is first formed upon substrate 22 and wherein well portion 38 is formed by electrically conductive material that is directionally deposited upon portion 36 at the same time that top electrode 32 is formed through the same directional deposition. In another implementation, well portion 38 may be omitted such as where top electrode 32 is formed through directional deposition such as sputtering or evaporation such that portion 36 provides the floor in electrical contact within the bottom of well 30. In one implementation, portion 36 of electrode 24 is joined to body 28 prior to the formation of well 30. In another implementation, portion 36 of electrode 24 is joined to body 28 after the formation of well 30.

Figure 3A:
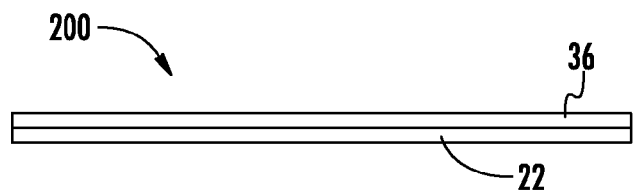
FIGS. 3A-3D are sectional views illustrating an example method for forming the electrochemical sensing cell of FIG. 1 by embossing.

FIGS. 3A-3D illustrate method 200, an example implementation of method 100, for forming cell 20 of FIG. 1. FIGS. 3A-3D illustrate formation of cell 20 comprising the step of embossing. As shown by FIG. 3A, bottom electrode portion 36 is formed upon substrate 22. In one implementation, substrate 22 is flexible and is provided from a roll. In one implementation, electrode portion 36 is also flexible and provided from a roll, wherein electrode portion 36 is laminated or otherwise joined to substrate 22. In yet another implementation, electrode portion 36 may be formed by spraying or coating electrically conductive material onto substrate 22. In some implementations, electrode portion 36 may be patterned using masks, photolithography or the like to form discrete portions or conductive traces on substrate 22.

Figure 3B:
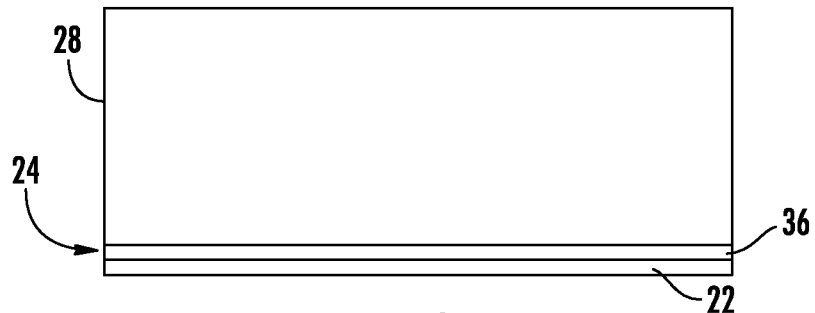
Figure 3C:
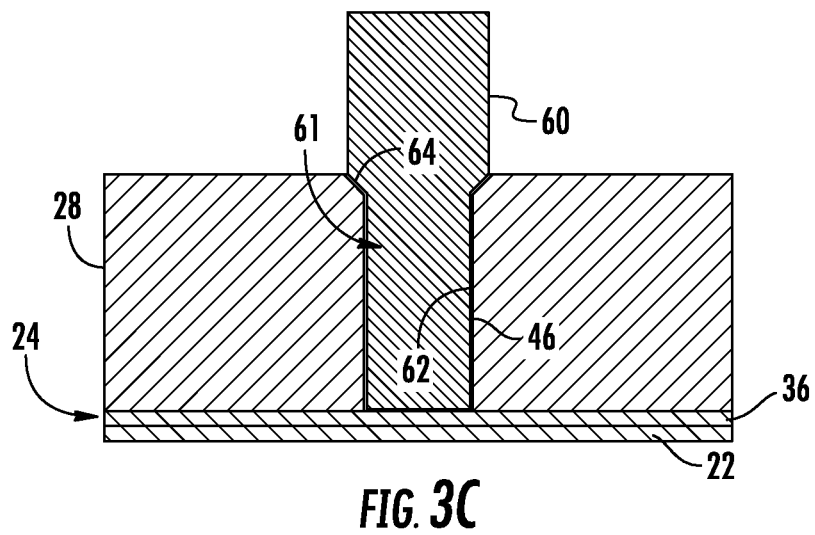

As shown by FIG. 3B, a volume or mass of embossable dielectric material providing body 28, such as an embossable resin, is formed on electrode portion 36, in contact with electrode portion 36. As shown by FIG. 3C, while body 28 is in an embossable state, an embossing tool 60 embosses body 28. Embossing tool 60 has an outer profile corresponding to the inner profile of well 30. In particular, tool 60 comprises a well forming projection 61 having a lower outer profile 62 shaped to form sidewalls 46 and an upper outer profile shaped to form chamfer 48. In one implementation, embossing tool 60 penetrates body 28 to a depth so as to contact and subsequently expose electrode portion 36 upon removal of embossing tool 60. In other implementations, material removal techniques may be employed to remove portions of body 28 at the bottom of the well 30 that cover electrode portion 36.

Figure 3D:
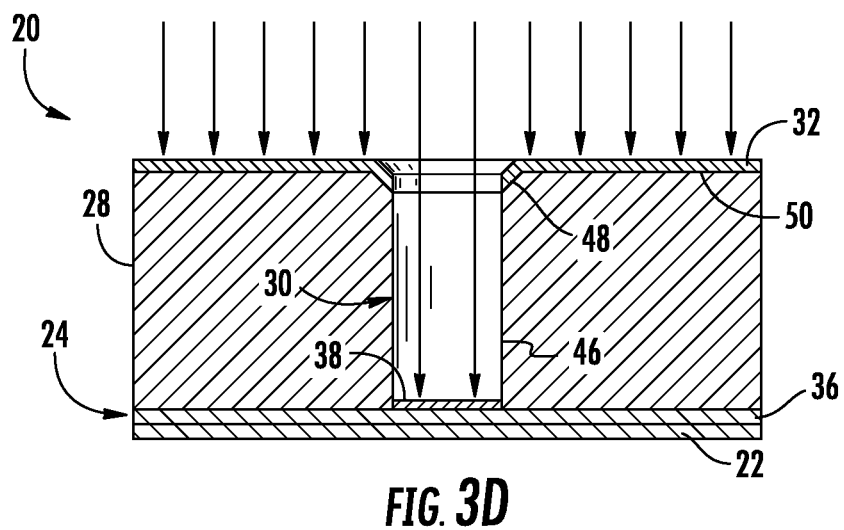

As shown by FIG. 3D, after embossing, body 28 is cured or otherwise solidified and embossing tool 60 is removed, leaving the formed well 30. In one implementation, such curing is achieved using ultraviolet light. In other implementations, depending upon the material forming body 28, body 28 may be cured or otherwise solidified in other fashions.

As further shown by FIG. 3D, electrically conductive material is directionally deposited in a direction parallel to sidewalls 46 of well 30 and upon electrode portion 36, upon top surface 50 of body 28 and upon chamfer 48 of well 30. Such directional deposition may be achieved using sputtering, evaporation or other directional deposition techniques. Because directional deposition is used, the electric conductive material becomes deposited upon electrode portion 36 as part of bottom electrode 24 and becomes deposited upon top surface 50 and chamfer 48 as part of top electrode 32. Top electrode 32 extends into well 30 by means of chamfer 48, but does not extend onto sidewalls 46 such that sidewalls 46 electrically isolate top electrode 32 from bottom electrode 24.

Although FIGS. 3A-3D illustrate the formation of an individual cell 20, method 200 may concurrently form an array of cells including cell 20. When forming such an array of cells 20, the steps shown in such FIGS. 3A-3D are substantially the same except that embossing tool 60 comprises an array of embossing projections corresponding to the array of wells 30 to be formed. The array of embossing projections concurrently or simultaneously emboss body 28 to form the array of wells, wherein the directional deposition step shown in FIG. 3D simultaneously or concurrently deposits electrically conductive material such that top electrode 32 extends into each of the wells 30 along each of the chamfers 48 of the wells 30. Overall, method 200 facilitates high precision and high-volume manufacture of an electrochemical sensing array of cells 20 into which chemicals in liquid or biological fluids may be easily introduced.

Figure 4A:
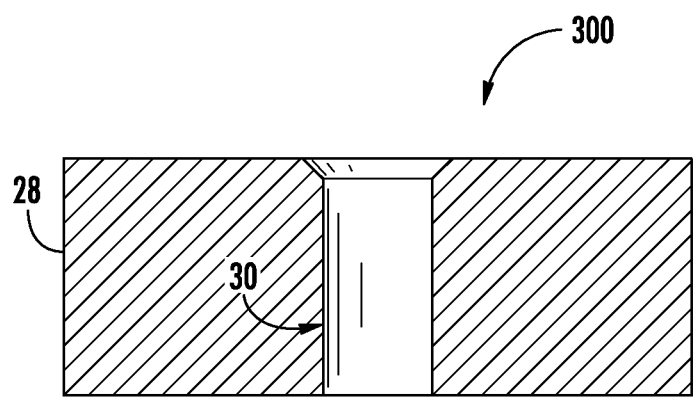
FIGS. 4A-4B are sectional views illustrating another example method for forming the electrochemical sensing cell of FIG. 1.
Figure 4B:
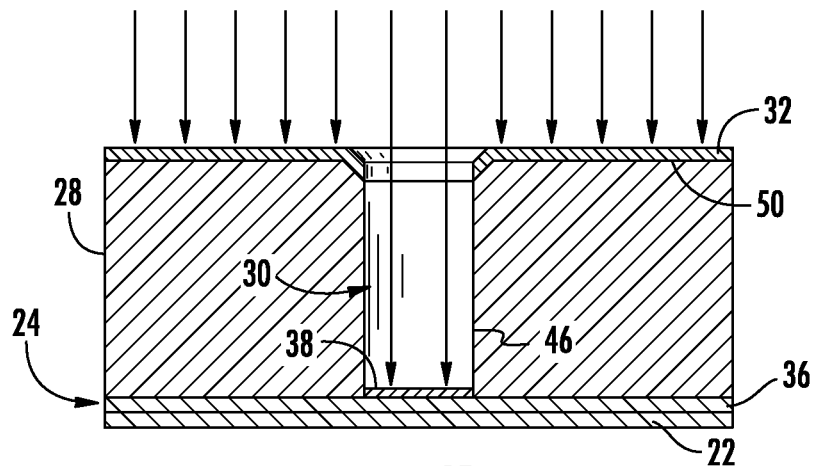

FIGS. 4A and 4B illustrate method 300, another example implementation of method 100 for forming electrochemical sensing cell 20 of FIG. 1, which may be part of a larger array of cells that are concurrently formed with the formation of the illustrated cell 20. As shown by FIG. 4A, well 30 is formed in body 28 prior to body 28 being joined to electrode portion 36 or substrate 22. In one implementation, well 30 is formed by embossing, wherein the lower supporting substrate is separated from body 28 upon completion of embossing. In another implementation, well 30 may be formed by photolithography, drilling, etching or other material removal techniques.

As shown by FIG. 4B, after the formation of well 30 and body 28, substrate 22 and electrode portion 36 of bottom electrode 24 are joined to body 28. As further shown by FIG. 4B, electrically conductive material is directionally deposited upon electrode portion 36, upon top surface 50 of body 28 and upon chamfer 48 of well 30 in a direction parallel to sidewalls 46 of well 30. Such directional deposition may be achieved using sputtering, evaporation or other directional deposition techniques. Because directional deposition is used, the electrically conductive material becomes deposited upon electrode portion 36 as part of bottom electrode 24 and becomes deposited upon top surface 50 and chamfer 48 as part of top electrode 32. Top electrode 32 extends into well 30 by means of chamfer 48, but does not extend onto sidewalls 46 such that sidewalls 46 electrically isolate top electrode 32 from bottom electrode 24.

Figure 5A:
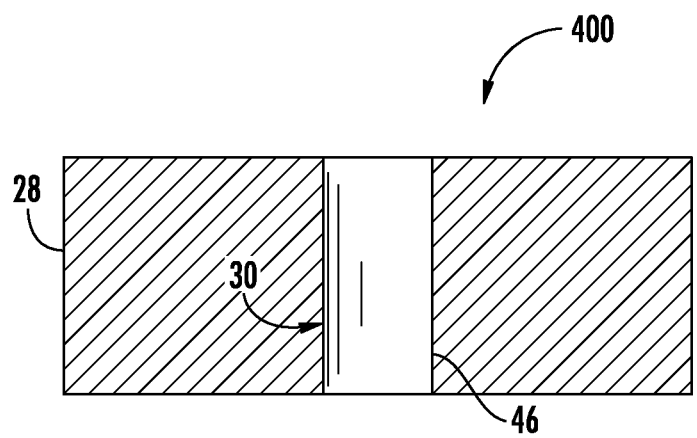
FIGS. 5A-5B are sectional views illustrating another example method for forming the electrochemical sensing cell of FIG. 1.
Figure 5B:
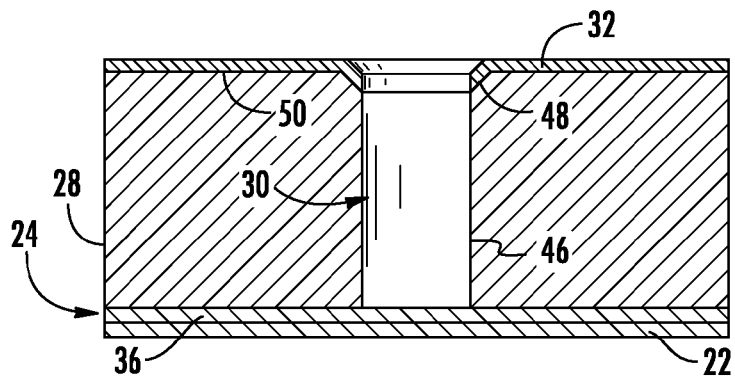

FIGS. 5A and 5B illustrate method 400, another example implementation of method 100 for forming electrochemical sensing cell 20 of FIG. 1, which may be part of a larger array of cells that are concurrently formed with the formation of the illustrated cell 20. As shown by FIG. 5A, well 30 is formed in body 28 prior to body 28 being joined to electrode portion 36 or substrate 22. Well 30 is formed in a two-step process. As shown by FIG. 5A, sidewalls 46 of well 30 are formed in body 28 prior to the formation of chamfers 28. In one implementation, sidewalls 46 are formed by embossing, drilling or other material removal techniques. In yet another implementation, sidewalls 46 may be formed by patterned material buildup of body 28 so as to form sidewalls 46.

As shown by FIG. 5B, chamfer 48 is subsequently formed in body 28 along an upper edge of sidewalls 46 near the top surface 50 of body 28. Chamfer 48 is formed using one or more material removal techniques such as etching, drilling, photolithography and the like. Body 28 is further joined to substrate 22 and electrode portion 36 of bottom electrode 24. After the formation of chamfer 48, electrically conductive material is directionally deposited upon electrode portion 36, upon top surface 50 of body 28 and upon chamfer 48 of well 30 in a direction parallel to sidewalls 46 of well 30. Such directional deposition may be achieved using sputtering, evaporation or other directional deposition techniques. Because directional deposition is used, the electric conductive material becomes deposited upon electrode portion 36 as part of bottom electrode 24 and becomes deposited upon top surface 50 and chamfer 48 as part of top electrode 32. Top electrode 32 extends into well 30 by means of chamfer 48, but does not extend onto sidewalls 46 such a sidewalls 46 electrically isolate top electrode 32 from bottom electrode 24.

Figure 6:
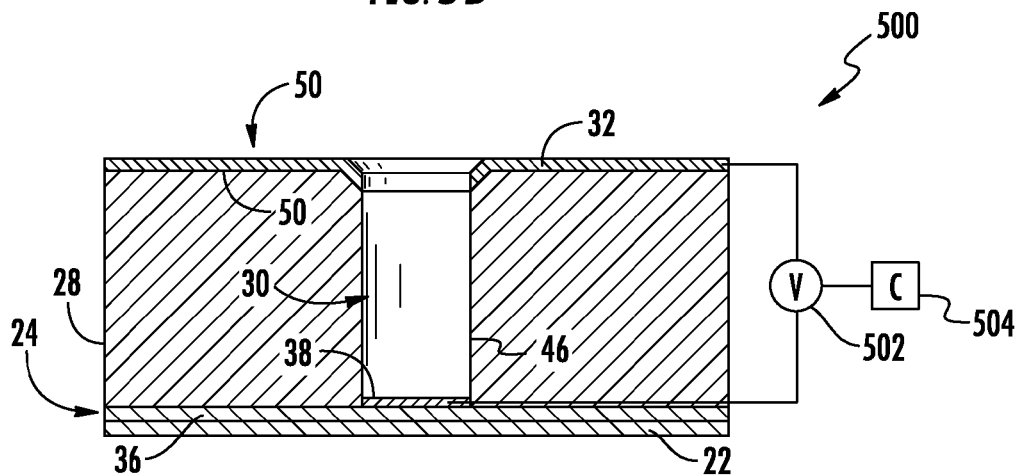
FIG. 6 is a sectional view illustrating an example electrochemical sensing system comprising the electrochemical sensing cell of FIG. 1.

FIG. 6 illustrates use of electrochemical sensing cell 20 as part of the electrical chemical sensing system 500. In addition to cell 20, system 500 comprises voltage source 502 and controller 504. Voltage source 502 comprise a source of electrical voltage connected to electrode 24 and 32 so as to apply an electric field to or through the analyte sample within well 30. In one implementation, one of electrodes 24, 32 may be electrically connected to ground while charge is applied to the other of electrodes 24, 32. In another implementation, different electrical charge may be applied to electrodes 24,32.

Controller 504 comprises one or more processing units configured to control the application of particular electric fields between electrodes 24, 32 designed to detect particular chemical species in the analyte sample (a particular buffered solution containing a chemical species) by controlling output of voltage source 502. Controller 504 is further configured to sense or detect impedance or other electrical characteristics to analyze the analyte sample within well 30. For example, controller 504 may determine or detect particular chemical species in an analyte sample based upon a detected electrical impedance of the analyte sample.

For purposes of this application, the term "processing unit" shall mean a presently developed or future developed processing unit that executes sequences of instructions contained in a non-transitory memory. Execution of the sequences of instructions causes the processing unit to perform steps such as generating control signals. The instructions may be loaded in a random access memory (RAM) for execution by the processing unit from a read only memory (ROM), a mass storage device, or some other persistent storage. In other embodiments, hard wired circuitry may be used in place of or in combination with software instructions to implement the functions described. For example, controller 504 may be embodied as part of one or more application-specific integrated circuits (ASICs). Unless otherwise specifically noted, the controller is not limited to any specific combination of hardware circuitry and software, nor to any particular source for the instructions executed by the processing unit.

Figure 7:
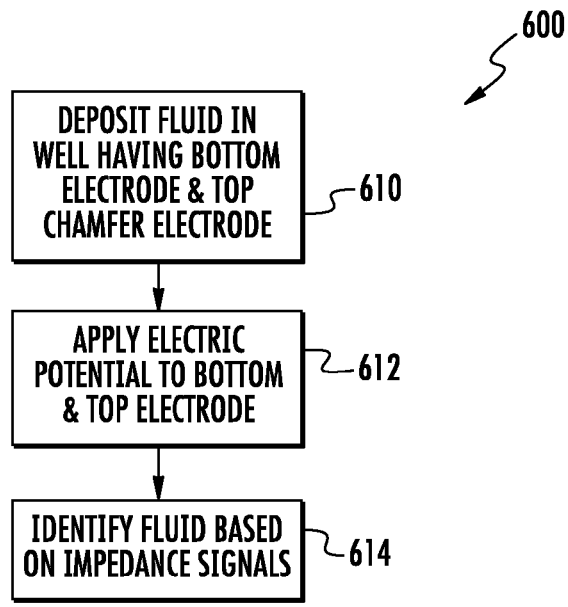
FIG. 7 is a flow diagram of an example method that may be carried out by the electrochemical sensing system of FIG. 6.

FIG. 7 is a flow diagram of an example method 600 that may be carried out by electrochemical sensing system 500 shown in FIG. 6. As indicated by step 610, the fluidic analyte sample is deposited in well 30 such that the analyte sample is in contact with both bottom electrode 24 and top electrode 32 along chamfer 48 of well 30. As indicated by step 612, controller 504, following instructions contained in a non-transitory memory, generates control signals causing voltage source 502 to apply charge or electric potential to at least one of electrodes 24, 32 to establish an electric field across the analyte sample within well 30. As indicated by step 614, controller 504 utilizes impedance signals and one or more electrochemical analytic techniques, such as electrochemical impedance spectroscopy, to sense or detect minute concentrations of chemical and/or biochemical species within the analyte sample. The detected chemical and/or biochemical species is an output via a display, print out or other output mechanism.

Figure 8:
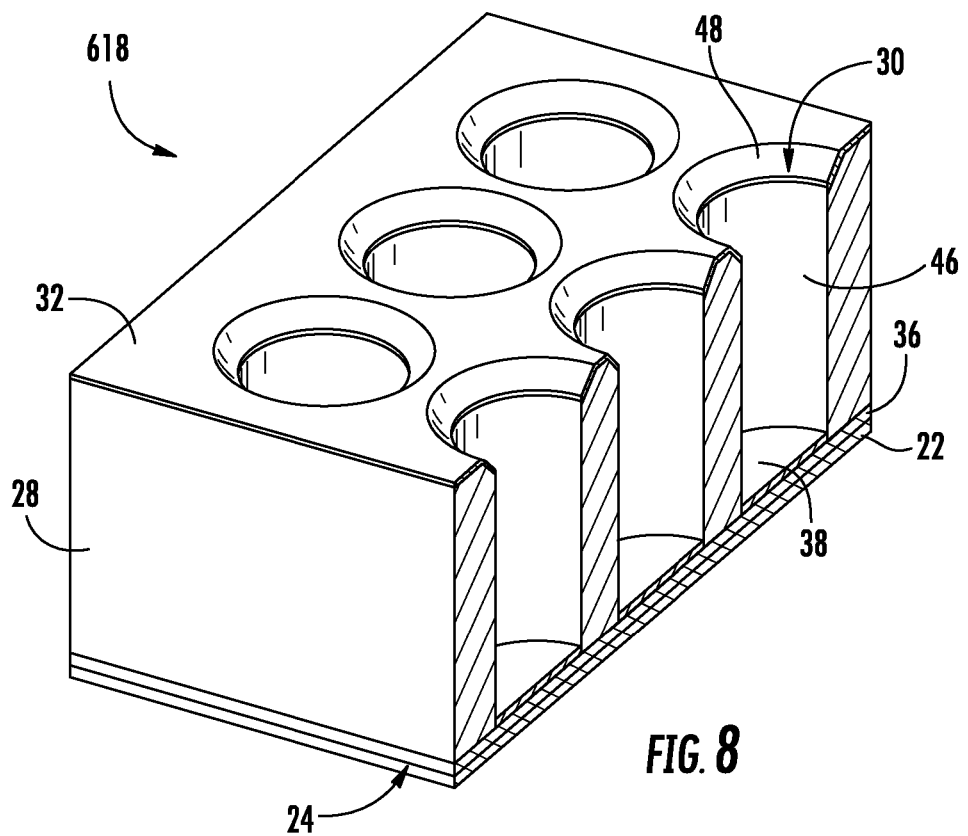
FIG. 8 is an isometric sectional view of an array of the electrochemical sensing cell of FIG. 1.
Figure 9:
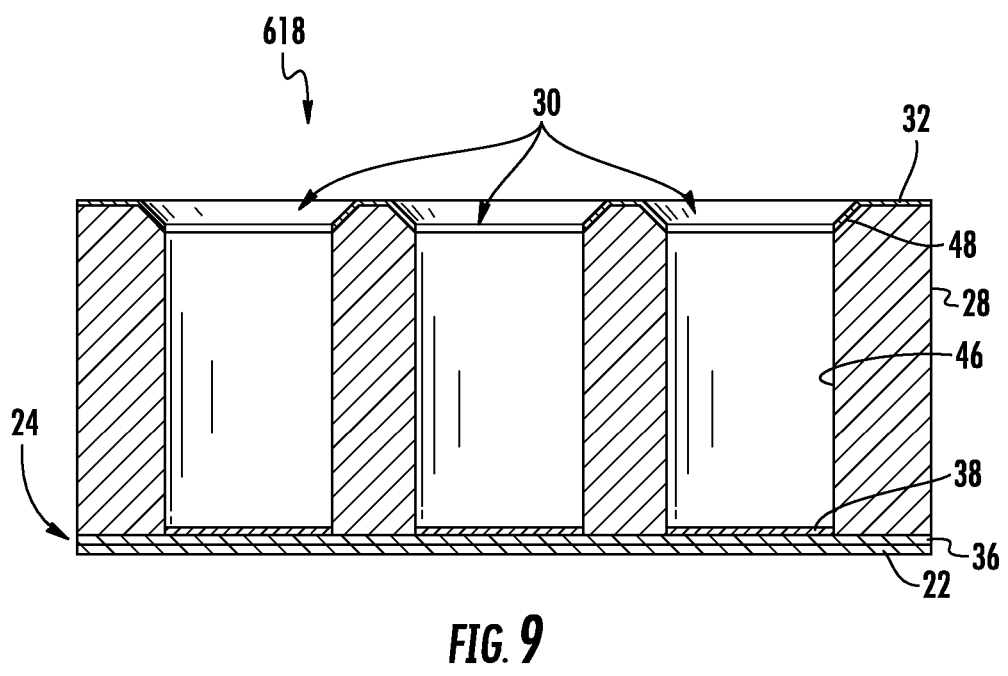
FIG. 9 is a sectional view of the array of FIG. 8.

FIGS. 8 and 9 illustrate an example array 618 of electrochemical sensing cells 20. FIG. 9 is a sectional view of the array 618 of electrochemical sensing cells 20. Array 618 may be formed by any of methods 100, 200, 300 and 400 described above. In one implementation, each of wells 30 of the cells 20 are concurrently formed, facilitating high-volume high precision manufacture of array 618. In other implementations, portions of array 618 may be formed at different times.

Figure 10:
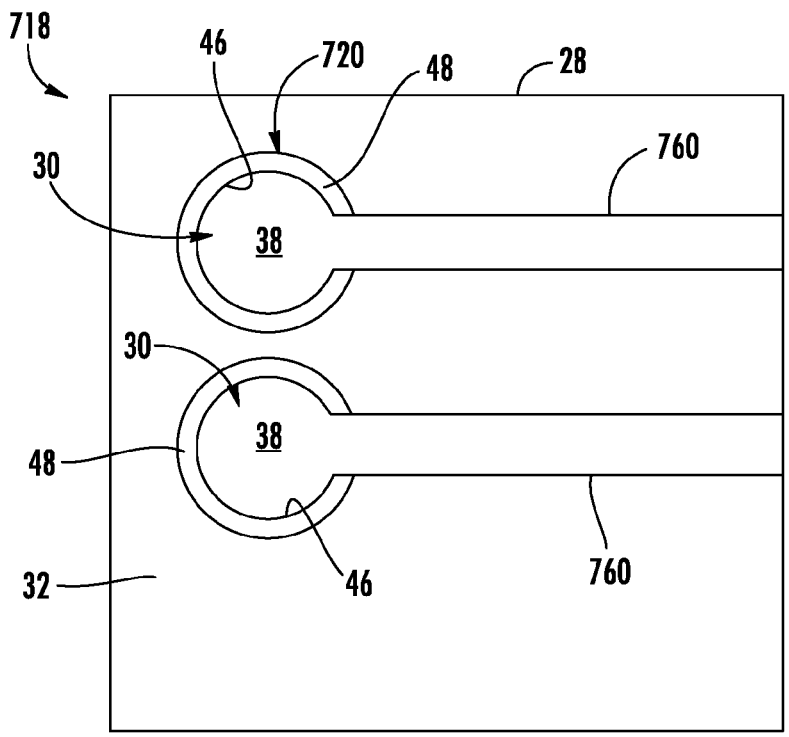
FIG. 10 is a top view of another example array of electrochemical sensing cells having fluidic channels.
Figure 11:
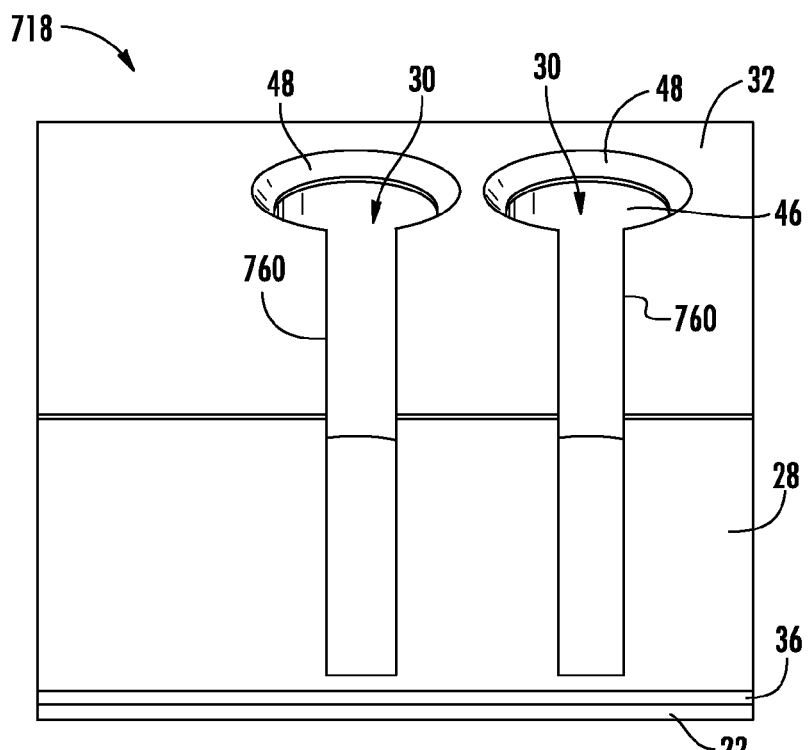
FIG. 11 is an isometric sectional view of the array of FIG. 10.

FIGS. 10 and 11 illustrate portions of an array 718 of electrochemical sensing cells 720. Each of cells 720 is similar to cell 20 described above except that each of cells 720 additionally comprises a fluidic channel 760. Fluidic channel 760 comprises a fluid passage extending through body 28 and opening into an interior of well 30. In the example illustrated, fluidic channel 760 is open along the top face of body 28 and open through top electrode 32. Fluidic channel 760 extends from the top face 50 of body 28 into body 28. In one implementation, fluidic channel 760 extends to electrode portion 36. In another implementation, fluidic channel 760 extends to substrate 22. In yet another implementation, fluidic channel 760 terminates so as to have a floor within body 28, spaced from electrode portion 36. In one implementation, the floor of fluidic channel 760 has deposited thereon electric conductive material from the directional deposition of top electrode 32.

Fluidic channel 760 facilitates filling and emptying of well 30 with the analyte sample. Fluidic channel 760 may further facilitate mixing of the analyte sample within well 30. Although illustrated as having straight or linear paths, fluidic channel 760 may alternatively be serpentine or of other path shapes. Although illustrated as having substantially vertical sidewalls, fluidic channel 76 may alternatively have angled or rounded sidewalls. Although fluidic channels 760 of the two illustrated cells 720 are illustrated as extending parallel to one another, in other implementations, fluidic channels 760 may have other paths to the respective wells 30.

Figure 12A:
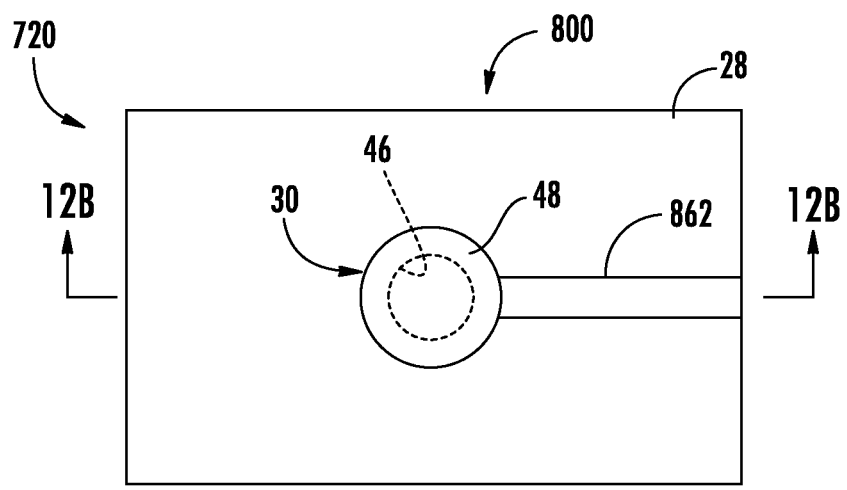
FIG. 12A is a top view illustrating embossing of the electrochemical sensing cell of FIG. 10.
Figure 12B:
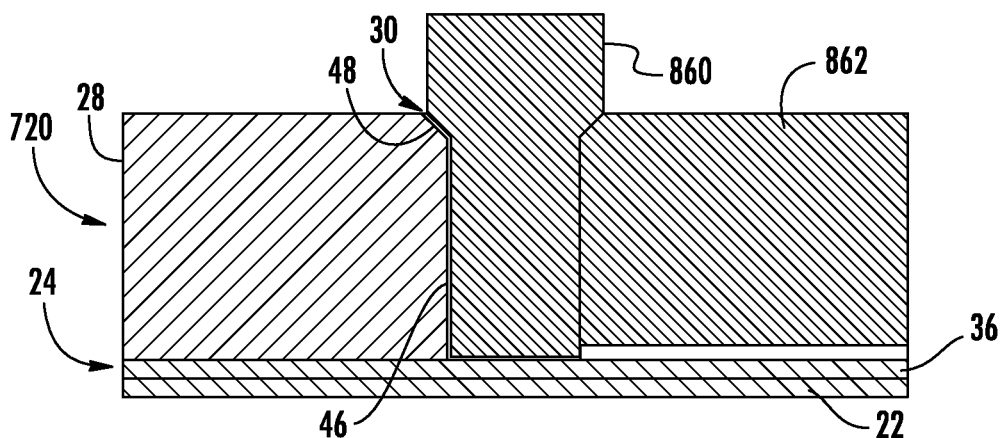
FIG. 12B is a sectional view illustrating the embossing of the electrochemical sensing cell of FIG. 12A.

FIGS. 12A and 12B illustrate an example method 800 for forming one of cells 720 by embossing. Similar to the embossment of cell 20 according to method 200 shown in FIGS. 3A and 3B, an embossable mass of material, such as an embossing resin, is formed upon electrode portion 36 and substrate 22 to form body 28. As shown by FIGS. 12A and 12B, well 30 and fluidic channel 760 are concurrently formed by embossing tool 860. Embossing tool 860 is similar to embossing tool 60 (shown in FIG. 3C) except that embossing tool 860 comprise an additional fluid channel forming extension portion 862. Upon insertion into the mass of embossment material forming body 28, fluid channel forming extension portion 862 embosses fluid channel 760 (shown in FIGS. 10 and 11). The remaining formation of cell 720 is similar to the steps shown in FIG. 3D above with respect to method 200. In particular, body 28 is cured or otherwise solidified, embossing tool 860 is removed and electrically conductive material is directionally deposited in a direction parallel to sidewalls 46 of well 30 to form electrode portion 38 in the bottom of well 30 and top electrode 32 extending on top surface 50 and chamfer 48 of well 30. Although FIGS. 12A and 12B illustrate the formation of a single one of cells 720, multiple cells 720 of array 718 may be concurrently formed using an embossing tool 860 which includes multiple projections and multiple portions 862 that are concurrently embossed into body 28.

Figure 13:
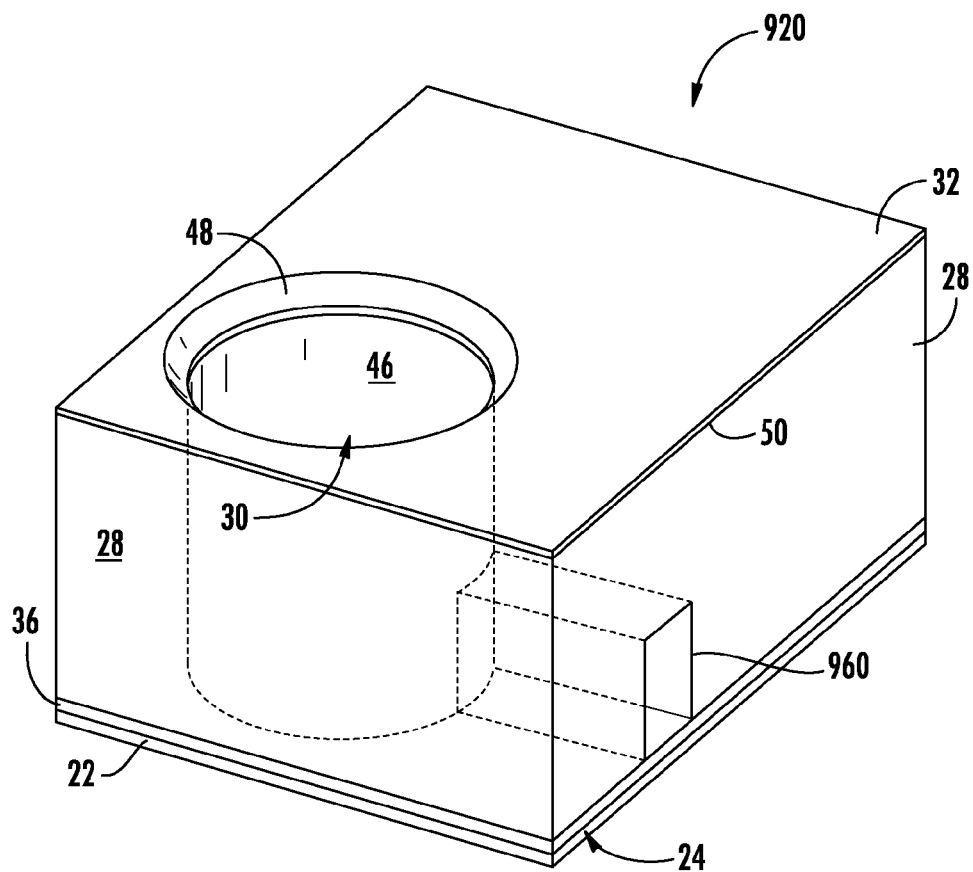
FIG. 13 is a top perspective view of another example electrochemical sensing cell.

FIG. 13 is a top perspective view of electrochemical sensing cell 920, another example implementation of electrochemical sensing cell 20. Electrochemical sensing cell 920 is similar to electrochemical sensing cell 720 except that electrode chemical sensing cell 920 comprises fluidic channel 960 in lieu of fluidic channel 760. Like fluidic channel 760, fluidic channel 960 comprises a fluid passage extending through body 28 and opening into an interior of well 30. In the example illustrated, fluidic channel 760 is surrounded but for an outer axial opening and an inner axial opening adjacent the interior of well 30. In the example illustrated, fluidic channel 960 is surrounded on three sides by body 28 and has a floor provided by electrode portion 36. In another implementation, channel 960 may have a floor provided by substrate 22. In other implementations, channel 960 may have the floor provided by body 28. Although illustrated as being linear and having a rectangular or square cross sectional shape, in other implementations, channel 960 may extend along other non-linear paths and have other cross-sectional shapes.

Fluidic channel 960 facilitates filling and emptying of well 30 with the analyte sample. Fluidic channel 960 may further facilitate mixing of the analyte sample within well 30.

Figure 14A:
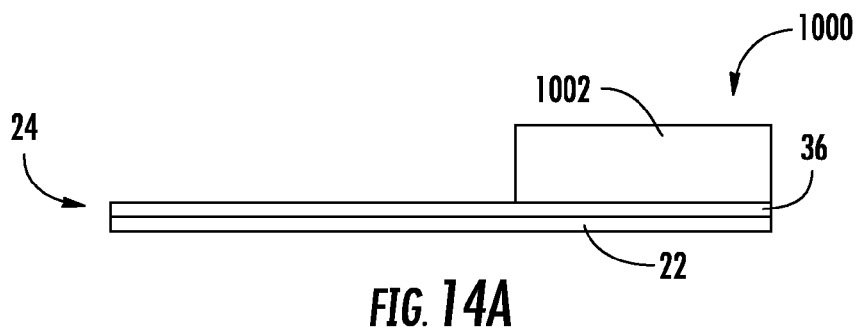
FIGS. 14A-14D are sectional views illustrating an example method of forming the electrochemical sensing cell of FIG. 13.

FIGS. 14A-14D illustrate an example method 1000 for forming one of cells 920 by embossing. As shown by FIG. 14A, bottom electrode portion 36 is formed upon substrate 22. In addition, a sacrificial core 1002 is formed upon the platform provided by bottom electrode portion 36 and substrate 22. In one implementation, sacrificial core 1002 is formed directly upon a top of electrode portion 36. In another implementation, sacrificial core 1002 may alternatively be formed directly upon a top of substrate 22, wherein electrode portion 36 is patterned around sacrificial core 1002. Sacrificial core 1002 has a negative shape corresponding to a shape of fluidic channel 960. Sacrificial core 1002 comprise a material that may be sacrificed or removed once body 28 has been solidified or cured to leave fluidic channel 960. In one implementation, sacrificial core 1002 comprises a material configured to be converted to a fluid state (liquid or gas) for removal. In another implementation, sacrificial core 1002 comprise a material configured to be etched, broken or shattered to facilitate such removal. In one implementation, the sacrificial core 1002 comprises a wax material that remains in a solid-state as the embossment material is formed or molded about sacrificial core 1002, wherein the wax composition forming the sacrificial core 1002 may subsequently be melted without melting, deforming or damaging the solidified or cured embossment material forming fluidic channel 960.

Figure 14B:
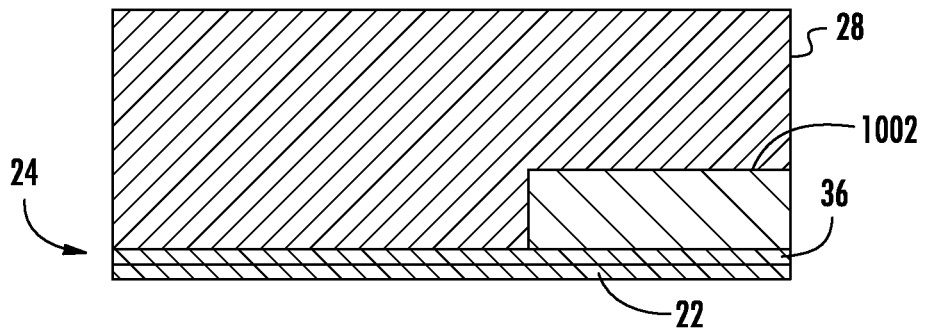
Figure 14C:
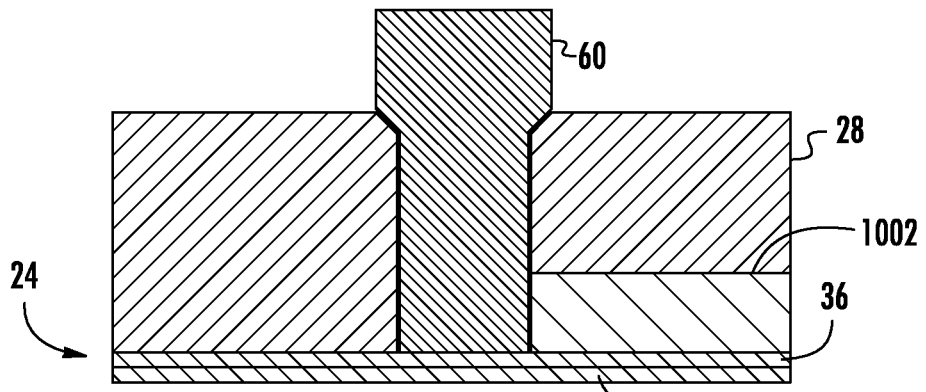

As shown by FIG. 14B, a volume or mass of embossable dielectric material providing body 28, such as an embossable resin, is formed on electrode portion 36, in contact with electrode portion 36 and about sacrificial core 1002. As shown by FIG. 14C, while body 28 is in an embossable state, an embossing tool 60 embosses body 28 adjacent to the sacrificial core 1002 such that the sacrificial core 1002 is exposed to the embossing tool 60. As a result, upon removal of embossing tool 60, sacrificial core 1002 is exposed to the interior of the formed well 30.

Embossing tool 60 has an outer profile corresponding to the inner profile of well 30. In particular, tool 60 has a lower outer profile 62 shaped to form sidewalls 46 and an upper outer profile before shaped to form chamfer 48. In one implementation, embossing tool 60 penetrates body 28 to a depth so as to contact and subsequently expose electrode portion 36 upon removal of embossing tool 60. In other implementations, material removal techniques may be employed to remove portions of body 28 at the bottom of the well 30 that cover electrode portion 36.

Figure 14D:
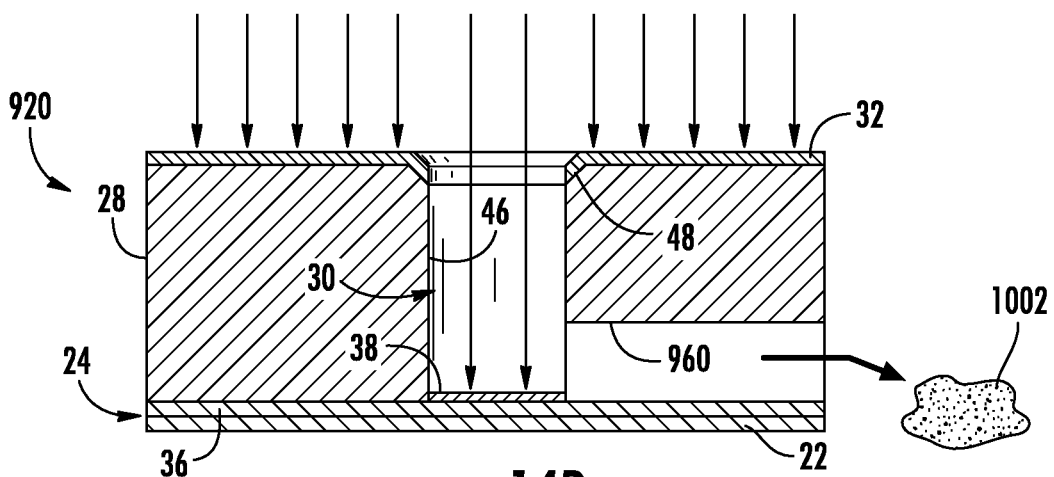

As shown by FIG. 14D, after embossing, body 28 is cured or otherwise solidified and embossing tool 60 is removed, leaving the formed well 30. In one implementation, such curing is achieved using ultraviolet light. In other implementations, depending upon the material forming body 28, body 28 may be cured or otherwise solidified in other fashions. Sacrificial core 1002 is exposed in the interior of well 30. In another implementation, sacrificial core 1002 may be sacrificed or removed prior to the removal of embossing tool 60.

As further shown by FIG. 14D, sacrificial core 1002 is sacrificed or removed, leaving fluidic channel 960. As noted above, in one implementation, sacrificial core 1002 is converted to a fluid state, or the fluid flows or is drawn from body 28. In another implementation, sacrificial core 1002 is etched away, broken or shattered to facilitate removal, leaving fluidic channel 960.

Prior to or following the sacrifice or removal of sacrificial core 1002, electrically conductive material is directionally deposited upon electrode portion 36, upon top surface 50 of body 28 and upon chamfer 48 of well 30 in a direction parallel to sidewalls 46 of well 30. Such directional deposition may be achieved using sputtering, evaporation or other directional deposition techniques. Because directional deposition is used, the electric conductive material becomes deposited upon electrode portion 36 as part of bottom electrode 24 and becomes deposited upon top surface 50 and chamfer 48 as part of top electrode 32. Top electrode 32 extends into well 30 by means of chamfer 48, but does not extend onto sidewalls 46 such a sidewalls 46 electrically isolate top electrode 32 from bottom electrode 24.

Although FIGS. 14A-14D illustrate the formation of an individual cell 920, method 200 may concurrently form an array of cells including cell 20. When forming such an array of cells 920, the steps shown in such FIGS. 14A-14D are substantially the same except that embossing tool 60 comprises an array of embossing projections corresponding to the array of wells 30 to be formed and that a plurality of sacrificial cores 1002 corresponding to the array of embossing projections and the array of wells 30 are formed upon the platform provided by substrate 22 and electrode portion 36. The array of embossing projections concurrently or simultaneously emboss body 28 to form the array of wells, wherein the directional deposition step shown in FIG. 14D simultaneously or concurrently deposits electrically conductive material such that top electrode 32 extends into each of the wells 30 along each of the chamfers 48 of the wells 30. Overall, method 1000 facilitates high precision high-volume manufacture of an electrochemical sensing array of cells 920 into which chemicals in liquid or biological fluids may be easily introduced through fluidic channel 960.

FIGS. 15-18 illustrate array 1118 of electrochemical sensing cells 1120, another example implementation of electrochemical sensing cell 20. Array 1118 is similar to array 718 (shown and described above with respect to FIGS. 10 and 11) except that array 1118 comprises electrochemical sensing cells 1120A and 1120B (collectively referred to as sensing cells 1120). Sensing cells 1120A and 1120B are similar to sensing cells 720 and 920, respectively, except that sensing cells 1120 each additionally comprise isolation walls 1170. Those remaining components of cells 1120A and 1120B which correspond to cells 720 and 920, respectively, are numbered similarly.

Isolation walls 1170 comprise walls extending outwardly from vertical walls 46 of wells 30, partitioning the otherwise continuous chamfer 48 of each well 30 into two or more separate chamfer portions, wherein the portions are spaced from one another by isolation walls 1170. Each of isolation walls 1170 comprises an electrical isolation surface continuously extending outwardly from sidewalls 46 of wells 30 and oriented so as to not receive the electrically conductive material during the directional deposition of top electrode 32. As a result, the electrical isolation surface electrically isolates electrical charge conducted to different portions of the same chamfer 48 about the same well 30, but for the conduction of electrical charge across any analyte sample within well 30 from one chamfer portion to another chamfer portion. Isolation walls 1170 facilitate the formation of multiple electrically distinct top electrodes 32 connected to a single well 30.

Figure 15:
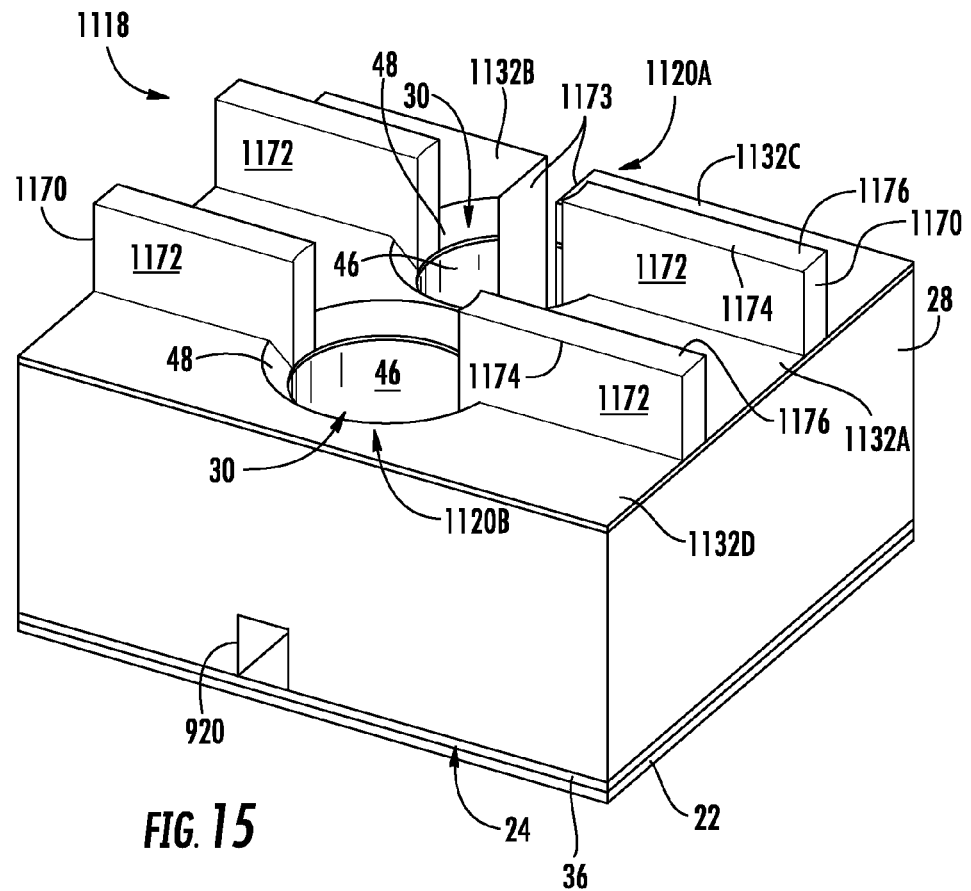
FIG. 15 is a top perspective view of another example array of electrochemical sensing cells.
Figure 16:
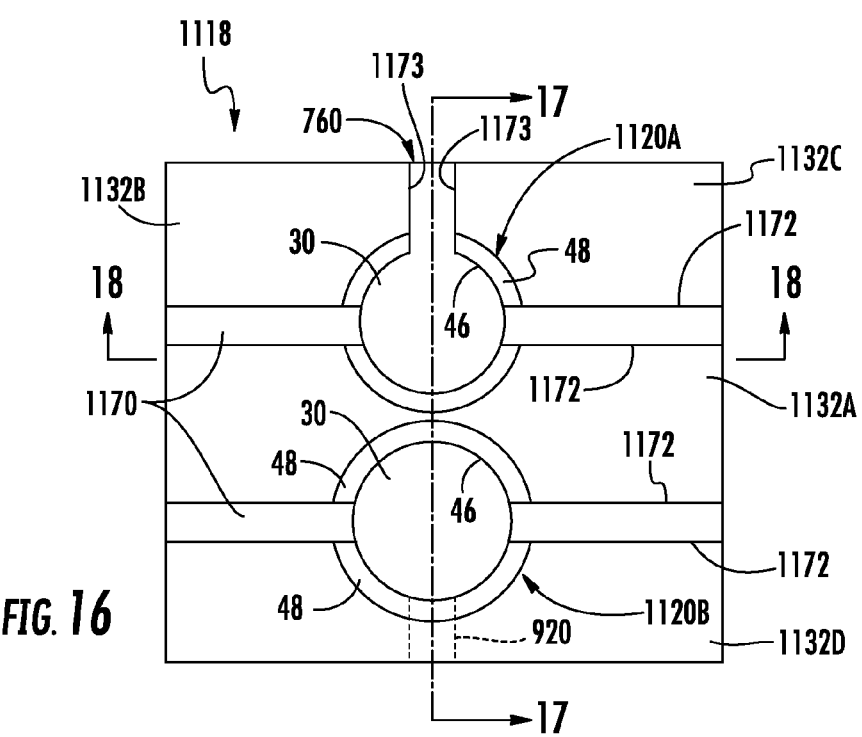
FIG. 16 is a top view of the array of FIG. 16.
Figure 17:
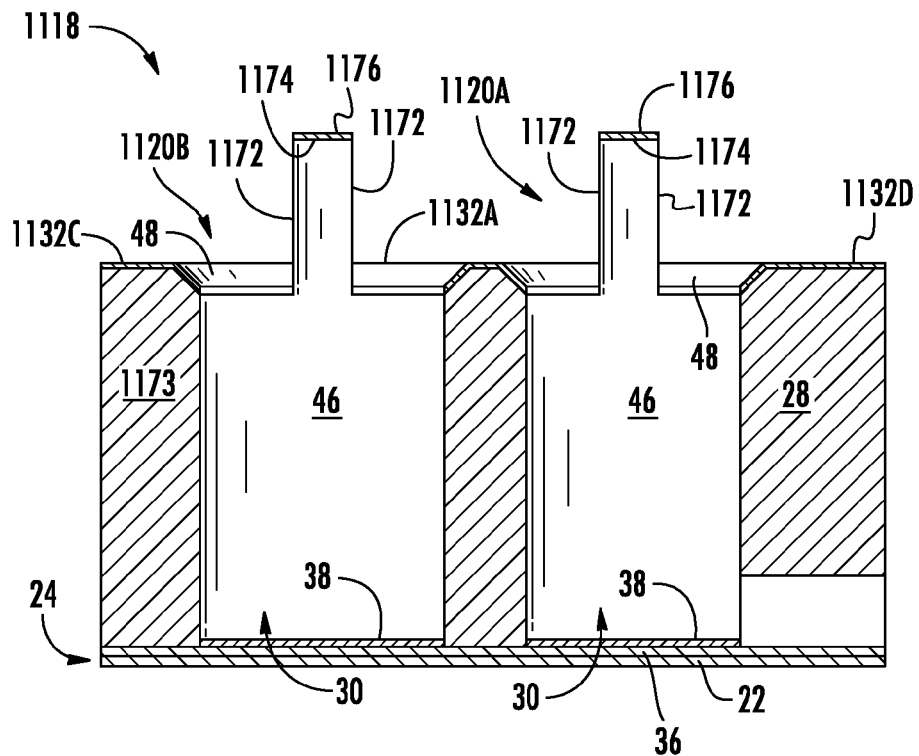
FIG. 17 is a sectional view of the array of FIG. 16 taken along line 17-17 of FIG. 16.
Figure 18:
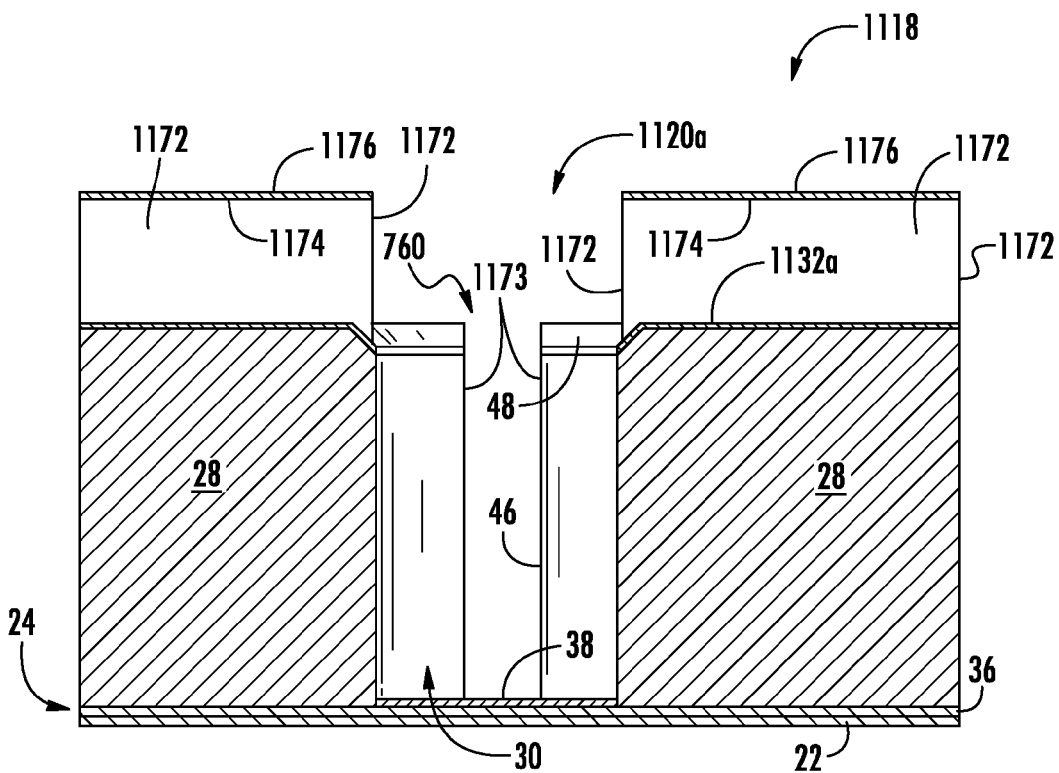
FIG. 18 is a sectional view of the array of FIG. 16 taken along line 18-18 of FIG. 16.

FIGS. 15-18 illustrate an example wherein each isolation wall 1170 has one or more isolation surfaces 1172 that extend parallel to sidewalls 46, wherein the isolation surfaces 1172 are located on an end of wall 1170 contiguous with sidewalls 46 and on one side of each wall 1170 or on both sides of each wall 1170. In the example illustrated, each isolation wall 1170 has two end vertical isolation surfaces 1172 and two opposite side vertical isolation surfaces 1170 perpendicular to top surface 50 that do not receive the electrically conductive material that is directionally deposited (in a direction parallel to sidewalls 46) during the formation of top electrode 32. As a result, as shown by FIGS. 15-17, each isolation wall 1170 further comprises a top surface 1174 upon which is deposited layer electrically conductive layer 1176 from the directional deposition of top electrode 32. However, the isolation surfaces 1172 electrically isolate the electrically conductive layer 1174 formed from the directionally deposited electrically conductive material on top surface 50 of body 28 forming top electrode 32.

As further shown by FIGS. 15-18, fluidic channel 760 in combination with isolation walls 1170 provide cell 1120A with three distinct, electrically isolated top electrodes 1132A, 1132B and 1132C, each of which may have a distinct electrical charge. Isolation walls 1170 electrically isolate one side of chamfer 48 of well 30 from the other side chamfer 48 of well 30 to electrically separate electrode 1132A from electrode 1132B and electrode 1132C. Fluidic channel 760 extends into body 28 through chamfer 48 and includes electrical isolation surface 1173. Similar to electrical isolation surfaces 1172, surface or surfaces 1173 extend parallel to sidewalls 46 of well 30 such that the directionally deposited (in a direction parallel to sidewalls 46) electrically conductive material forming top electrode 1132B and 1132C is not deposited upon surfaces 1173. As a result, surfaces 1173 further partition chamfer 48 into electrically distinct regions upon which electrically distinct electrodes 1132B and 1132C are formed. As noted above, fluidic channel 760 further facilitates filling, emptying or mixing of an analyte sample within the associated well 30. In other implementations, fluidic channel 760 may be shallower or may not be used to move analyte into and/or out of well 30, but may be merely provided for further electrically partitioning chamfer 48 to provide additional electrically distinct electrodes for the particular well 30.

As shown by FIG. 15, isolation walls 1170 further partition well 30 of cell 1120B into two distinct top electrodes 1132A and 1132D. Because cell 1120B includes fluidic channel 920 which does not electrically partition chamfer 48 of cell 1120B, analyte may be supplied to, withdrawn from or mixed within well 30 of cell 1120B, while providing 1120B with two, rather than three top electrodes. In other implementations, one or both of fluidic channels 720, 920 may be omitted.

FIGS. 19A-19E illustrate an example method 1200 for forming cell 1120A of array 1118. Method 1200 may be utilized to concurrently form cell 1120B with the cell 1120A, where cell 1120B is formed by concurrently forming the same embossable material forming body 28 about cell 1120A about sacrificial core 1002 and subsequently sacrificing sacrificial core 1002 as described above with respect to FIGS. 14C and 14D. In other implementations, array 1118 may include an array of just cells 1120A or an array of just cells 1120B.

Figure 19A:
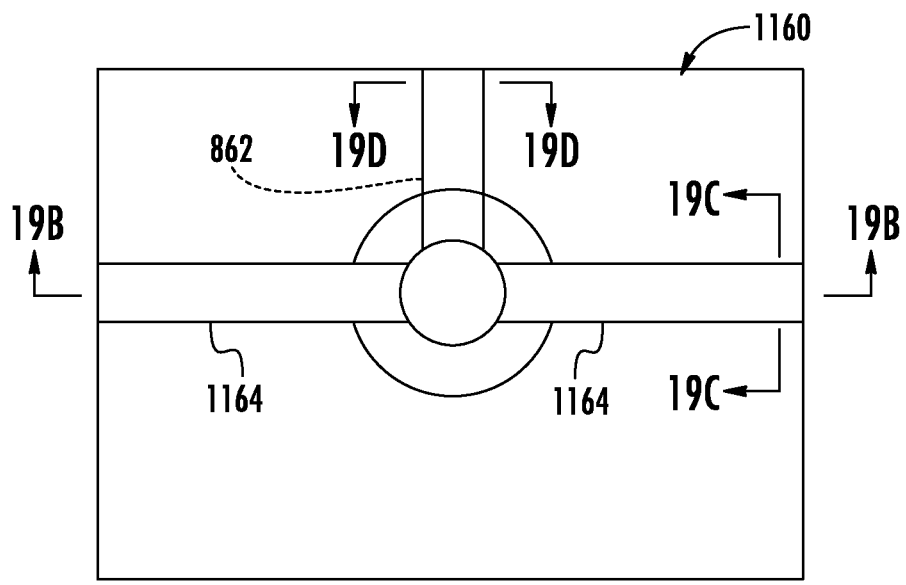
FIG. 19A is a bottom view of an example embossing tool for embossing and electrochemical sensing cell of the array of FIG. 15.
Figure 19B:
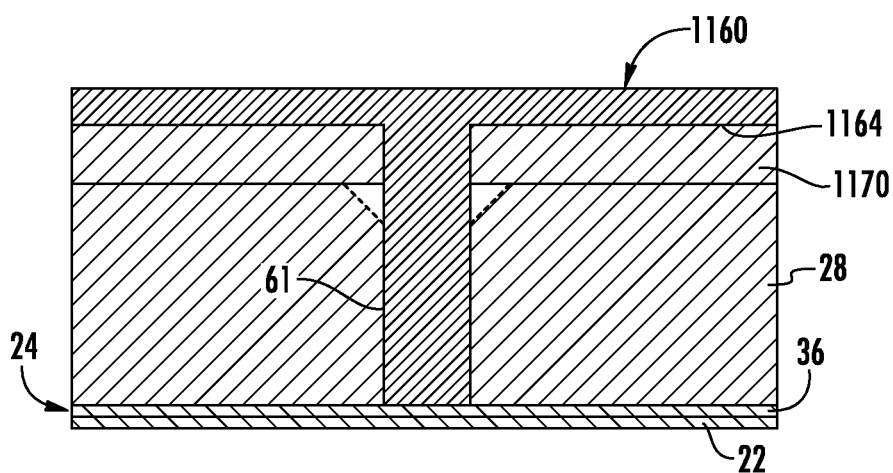
FIG. 19B is a sectional view illustrating embossment of the cell of FIG. 15 taken along line 19B-19B of the tool of FIG. 19A.
Figure 19C:
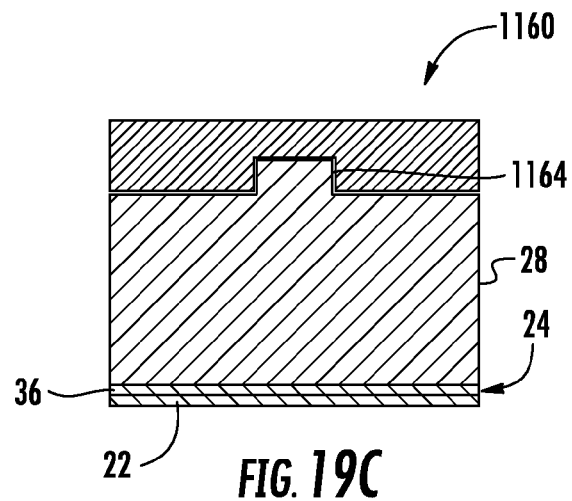
FIG. 19C is a sectional view illustrating embossment of the cell of FIG. 15 taken along line 19C-19C of the tool of FIG. 19A.
Figure 19D:
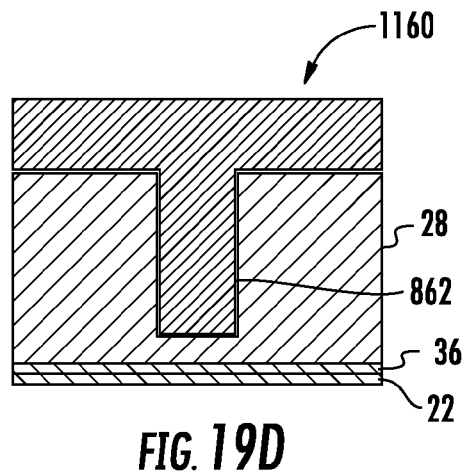
FIG. 19D is a sectional view illustrating embossment of the cell of FIG. 15 taken along line 19D-19D of the tool of FIG. 19A.

As shown by FIGS. 19A-19C, well 30, fluidic channel 760 and isolation walls 1170 are concurrently formed by embossing tool 1160. FIG. 19A is a bottom view of embossing tool 1160. FIGS. 19B-19D illustrate the bottom of embossing tool 1160 pressed into or embossing body 28 while body 28 is in an embossable state. Embossing tool 1160 is similar to embossing tool 860 (shown in FIGS. 12A and 12C) except that, in addition to comprising extension 862 projecting from a bottom of embossing tool 1160 and from the well forming portion 61, embossing tool 1160 comprises additional channels 1164 extending into a bottom surface of embossing tool 1160 for forming isolation walls 1170. Upon the depressment into the mass of embossment material forming body 28, fluid channel forming extension portion 862 embosses fluid channel 760 (shown in FIG. 15). Channels 1164 are filled with the embossable material of body 28 to form isolation walls 1170.

Figure 19E:
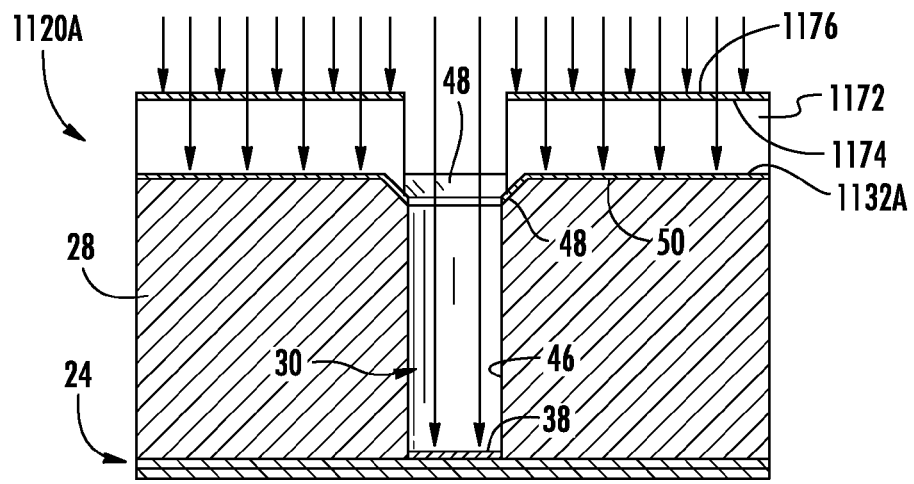
FIG. 19E is a sectional view illustrating deposition of electrodes on the embossed cell of FIG. 15.

The remaining formation steps for forming cell 1120A is similar to the steps shown in FIG. 3D above with respect to method 200 and shown in FIG. 19E. In particular, body 28 is cured or otherwise solidified, embossing tool 1160 is removed and electrically conductive material is directionally deposited in a direction parallel to sidewalls 46 of well 30 to form electrode portion 38 in the bottom of well 30 and top electrodes 1132A-1132C extending on top surface 50 and chamfer 48 of well 30 of cell 1120A. Although FIGS. 12A and 12B illustrate the formation of a single one of wells 720, multiple wells 1120A (or 1120B) of array 1118 may be concurrently formed using an embossing tool 1160 which includes multiple well forming projections 61, multiple fluidic channel forming portions 862 and multiple isolation walls forming portions or channels 1164 that are concurrently embossed into body 28.

Figure 20:
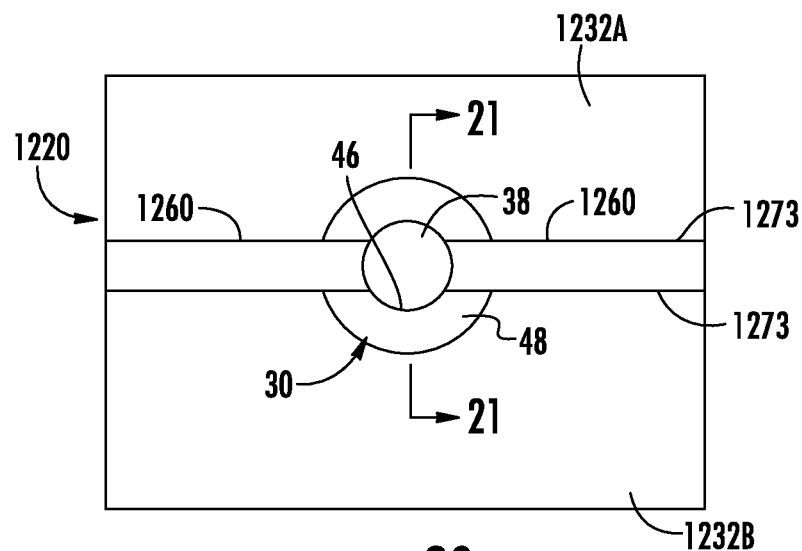
FIG. 20 is a top plan view of another example electrochemical sensing cell.
Figure 21:
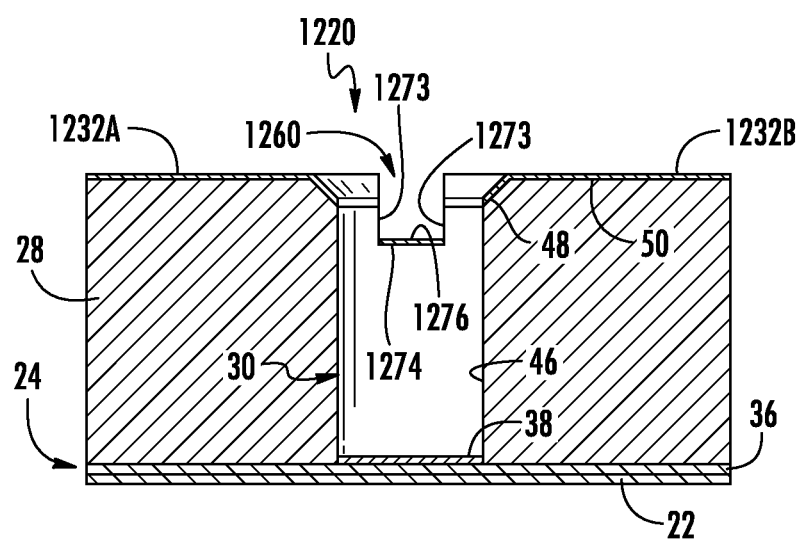
FIG. 21 is a sectional view of the electrochemical sensing cell of FIG. 20 taken along line 21-21.

FIGS. 20 and 21 illustrate electrochemical sensing cell 1220, another example implementation of electrochemical sensing cell 20. Electrochemical sensing cell 1220 is similar to electrochemical sensing cell 20 except that cell 1220 additionally comprises isolation channels 1260. Those remaining components of cell 1220 which correspond to components of cell 20 are numbered similarly.

Isolation channels 1260 comprise grooves or channels extending outwardly from vertical walls 46 of wells 30, partitioning the otherwise continuous chamfer 48 of well 30 into two or more separate chamfer portions, wherein the chamfer portions are spaced from one another by isolation channels 1260. Each of isolation channels 1260 comprises an electrical isolation surface continuously extending outwardly from sidewalls 46 of wells 30 so as to not receive the electrically conductive material during the directional deposition of top electrode 32. As a result, the electrical isolation surface electrically isolates electrical charge conducted to different portions of the same chamfer 48 about the same well 30, but for the conduction of electrical charge across any analyte sample within well 30 from one chamfer portion to another chamfer portion. Isolation channels 1260 facilitate the formation of multiple electrically distinct top electrodes 32 connected to a single well 30.

FIGS. 20 and 21 illustrate an example wherein each isolation channel 1260 has one or more isolation surfaces 1273 that extend parallel to sidewalls 46, wherein the isolation surfaces 1273 are located on one side of each channel 1260 or on both sides of each channel 1260. In the example illustrated, each isolation channel 1260 has two opposite side vertical isolation surfaces 1273 perpendicular to top surface 50 that do not receive the electrically conductive material that is directionally deposited (in a direction parallel to sidewalls 46) during the formation of top electrode 32. As a result, as shown by FIG. 21, each isolation channel 1260 further comprises a floor 1274 upon which is deposited layer electrically conductive layer 1276 from the directional deposition of top electrode 32. However, the isolation surfaces 1273 electrically isolate the electrically conductive layer 1274 formed from the directionally deposited electrically conductive material on top surface 50 of body 28 forming top electrodes 1232A and 1232B. Each of isolation channels 1260 may be formed utilizing the method illustrated in FIGS. 12A and 12B and utilizing an embossing tool similar to embossing tool 860 but including an additional oppositely extending extension 862.

Figure 22:
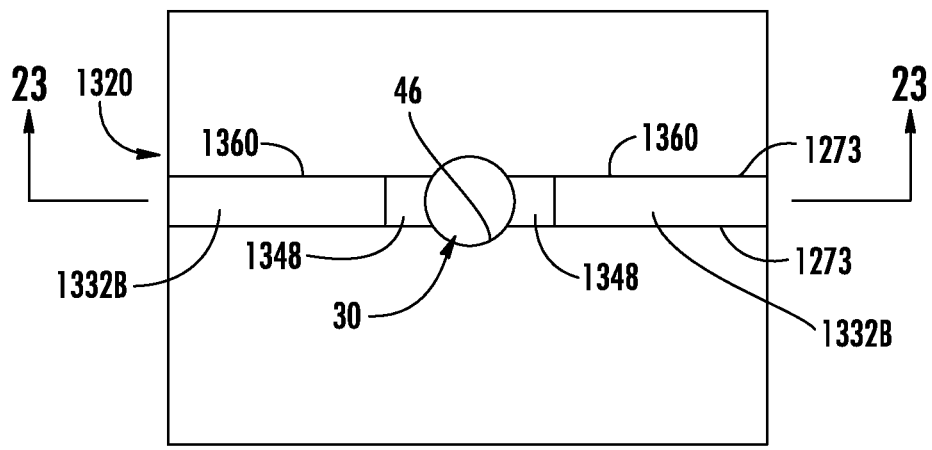
FIG. 22 is a top plan view of another example electrochemical sensing cell.
Figure 23:
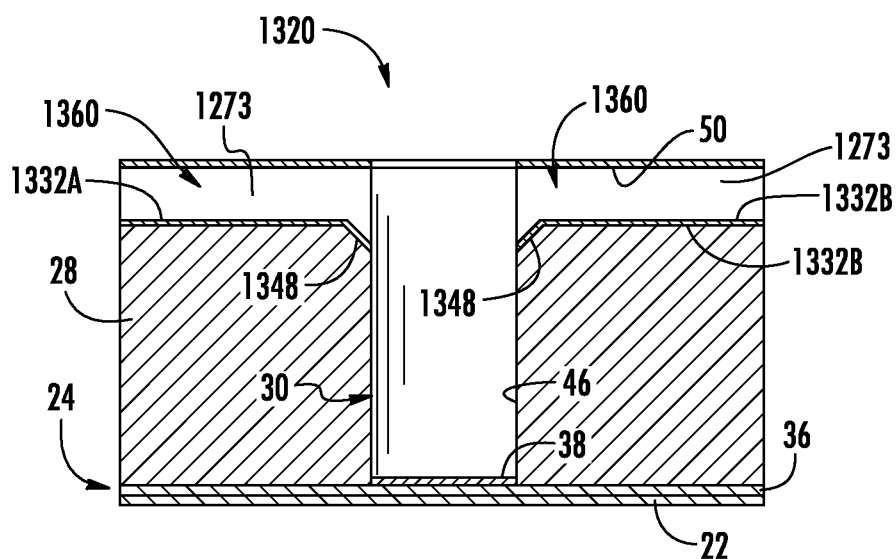
FIG. 23 is a sectional view of the electrochemical sensing cell of FIG. 22 taken along line 23-23.

FIGS. 22 and 23 illustrate electrochemical sensing cell 1320, another example implementation of electrochemical sensing cell 20. Electrochemical sensing cell 1320 is similar to electrochemical sensing cell 1220 except that cell 1320 comprises channels 1360 and chamfer 1348 in place of channels 1260 and chamfer 48, respectively. Those remaining components of cell 1320 which correspond to components of cell 1220 are numbered similarly.

Channels 1360 are similar to channels 1260 except that channel 1360 terminate at chamfer 1348 of well 30. As with channels 1260, channels 1360 comprise isolation surfaces 1273 which extend parallel to sidewalls 46 and which do not receive electrically conductive material during directional deposition of the electrically conductive material. Chamfer 1348 is similar to chamfer 48 except that chamfer 1348 is provided at the ends of channels 1360. In contrast to chamfer 48 which is located at a top of well 30 between sidewalls 46 of well 30 and top surface 50 of body 28, chamfer 1348 is located between sidewalls 46 of well 30 and floor 1274 of each of channels 1360. During directional deposition of electrically conductive electrode material, the electrically conductive material is deposited upon chamfer 1348 as well of floor 1274 of channels 1360 to form top electrodes, a first top electrode 1332A extending along one of channels 1360 and a second top electrode 1332B extending along the other of channels 1360. Isolation surfaces 1273 serve to electrically isolate electrodes 1332A and 1332B from one another. During use, well 30 is filled with the liquid analyte sample to a level above a lower end of chamfer 1348, wherein distinct electrical fields may be applied to the analyte sample within well 30 using either of electrodes 1332A, 1332B. Chamfer 1348 may be formed by embossing or any of the aforementioned methods.

Each of isolation walls 1170 and isolation channels 1260 (as well as fluidic channel 760 in cell 1120A) have isolation surfaces that are parallel to sidewalls 46 such that the electrically conductive material directionally deposited to form the top electrode(s) is not deposited upon such isolation surfaces. FIGS. 22 and 23 illustrate alternative isolation surfaces wherein such isolation surfaces are not parallel to sidewalls 46 of well 30, but extend below notches or undercuts such that directionally deposited electrically conductive material does not form thereon such that electrical isolation is achieved to electrically partition chamfer 48 and electrically conductive material on top 50 of body 28 into multiple electrodes.

Figure 24:
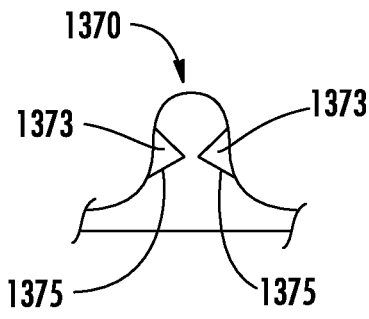
FIG. 24 is a sectional view of example isolation wall of an electrochemical sensing cell.

FIG. 24 illustrates isolation wall 1370 having isolation surface 1373 formed in a notch or cut out 1375. In one implementation, the notch or cut out 1375 may continuously extend about end of wall 1370 adjacent well 30. In another implementation, wall 1370 may have surface that is parallel to sidewalls 46. During directional deposition of the top electrode(s), electrically conductive material is not deposited upon isolation surface 1373.

Figure 25:
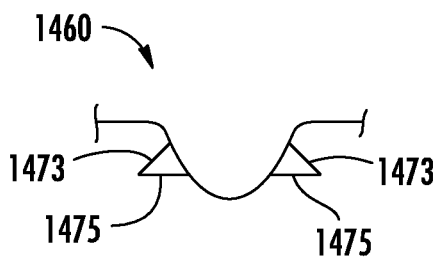
FIG. 25 is a sectional view of an example isolation channel of an electrochemical sensing cell.

FIG. 25 illustrates isolation channel 1460. Isolation channel 1460 similar to isolation channel 1260 except that isolation channel 1460 has isolation surface 1473 formed in a cut outer notch 1475. During directional deposition of the top electrode(s), electrically conductive material is not deposited upon isolation surface 1473. Using one or both of isolation walls 1374 of isolation channels 1460, an electrochemical sensing cell may be electrically partitioned to provide a plurality of electrodes for a single well 30. Although not illustrated, each of the aforementioned electrochemical sensing cells is employed as part of electrochemical sensing system comprising voltage source 502 and controller 504 shown and described above with respect to FIG. 6 for carrying out the method 600 shown and described with respect to FIG. 7.

Although the present disclosure has been described with reference to example embodiments, workers skilled in the art will recognize that changes may be made in form and detail without departing from the spirit and scope of the claimed subject matter. For example, although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described with reference to the example embodiments and set forth in the following claims is manifestly intended to be as broad as possible. For example, unless specifically otherwise noted, the claims reciting a single particular element also encompass a plurality of such particular elements.

What is claimed is:

1. A method comprising:
    forming an array of open wells in a body, each of the wells having a chamfered edge about a top side of the well;
    directionally depositing an electrode material on the top surface of the body and the chamfered edge of each of the wells to form a top electrode layer; and
    providing a bottom electrode on a bottom of the wells,
    providing a non-conductive sidewall in each of the wells to electrically isolate the top electrode layer from the bottom electrode, the non-conductive sidewall to extend from the bottom electrode to the chamfered edge.

2. The method of claim 1, wherein the electrode material is directionally deposited using a technique selected from a group of directional deposition techniques consisting of sputtering and evaporation.

3. The method of claim 1 further comprising forming a fluidic channel in the body in communication with an interior of one of the wells.

4. The method of claim 1, wherein the open wells are formed by embossing into the top face of the body.

5. The method of claim 1 further comprising:
    embossing a fluidic channel into a bottom face of the body; and
    forming a bottom electrode layer across the bottom face of the body over the fluidic channel.

6. The method of claim 5, wherein the fluidic channel is filled with a sacrificial core during formation of the bottom electrode layer, the method further comprising removing the sacrificial core to clear the fluidic channel.

7. The method of claim 1 further comprising:
    forming a first electrical isolation surface along the top face outwardly from the well; and
    forming a second electrical isolation surface along the top face outwardly from the well, the first electrical isolation surface and the second electrical isolation surface dividing the top electrode layer into electrically distinct electrodes connected to the well.

8. The method of claim 1, wherein the sidewall extends substantially perpendicularly from the bottom of each well to the chamfered edge.

9. The method of claim 1, wherein each of the open wells is to receive a fluidic analyte sample.

10. The method of claim 1, wherein the top electrode layer extends circumferentially around the top surface and chamfered edge of each of the wells.

11. The method of claim 1, wherein the top and bottom electrodes are each connected to a voltage source such that an electrical potential is established between the top and bottom electrodes.

* * * * *

UNITED STATES PATENT AND TRADEMARK OFFICE
CERTIFICATE OF CORRECTION

PATENT NO. : 9,557,288 B2
APPLICATION NO. : 13/873199
DATED : January 31, 2017
INVENTOR(S) : James Elmer Abbott et al.

It is certified that error appears in the above-identified patent and that said Letters Patent is hereby corrected as shown below:

On the Title Page

In item (72), Inventors, in Column 1, Line 4, delete "Covallis," and insert -- Corvallis, --, therefor.

Signed and Sealed this
Thirtieth Day of May, 2017

Michelle K. Lee
*Director of the United States Patent and Trademark Office*